United States Patent
Favreau et al.

(10) Patent No.: US 12,364,616 B2
(45) Date of Patent: Jul. 22, 2025

(54) DEVICES, SYSTEMS, AND METHODS FOR ADJUSTING A PASSAGE THROUGH AN IMPLANTABLE DEVICE

(71) Applicant: BOSTON SCIENTIFIC SCIMED, INC., Maple Grove, MN (US)

(72) Inventors: John Thomas Favreau, Spencer, MA (US); Andrew Pic, Northboro, MA (US); Joseph W King, Franklin, MA (US); Lauren Sfakis Lydecker, Millbury, MA (US); Travis Henchie, Worcester, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 179 days.

(21) Appl. No.: 17/747,344

(22) Filed: May 18, 2022

(65) Prior Publication Data
US 2022/0370222 A1  Nov. 24, 2022

Related U.S. Application Data

(60) Provisional application No. 63/190,545, filed on May 19, 2021.

(51) Int. Cl.
*A61F 5/00*  (2006.01)

(52) U.S. Cl.
CPC .......... *A61F 5/0076* (2013.01); *A61F 5/0089* (2013.01)

(58) Field of Classification Search
CPC .... A61F 5/0076; A61F 5/0089; A61F 5/0079; A61F 2250/0007; A61B 2017/1139; A61B 17/1114; A61B 17/12118; A61B 17/12159

See application file for complete search history.

(56) References Cited

U.S. PATENT DOCUMENTS 3,942,407 A * 3/1976 Mortensen ............ F16B 37/067
  411/36
9,707,124 B2 * 7/2017 Brenzel ............ A61B 17/12172
(Continued)

FOREIGN PATENT DOCUMENTS

JP  2009509669 A  3/2009
JP  2018501050 A  1/2018
(Continued)

OTHER PUBLICATIONS

Invitation to Pay Additional Fees dated Aug. 22, 2018 for International Application No. PCT/US2022/029792.

*Primary Examiner* — Kai H Weng
*Assistant Examiner* — Alessandro R Del Priore
(74) *Attorney, Agent, or Firm* — Seager, Tufte & Wickhem, LLP

(57) ABSTRACT

An implantable device having an adjustable passage therethrough. The passage may be adjustable to occlude or otherwise to regulate access or flow of materials therethrough. An elongated element may be inserted into the passage when in a closed configuration to selectively open the passage. For instance, the implantable device may be a tubular device with a twisted region closing the passage therethrough, and the elongated device may be configured to engage such twisted region and to be rotated to untwist the closed region. An additional tubular device with a passage therethrough may be inserted into the passage of the implantable device to hold open the passage for a selected period of time.

20 Claims, 6 Drawing Sheets

(56) References Cited

U.S. PATENT DOCUMENTS

| | | |
|---|---|---|
| 9,774,062 B2 | 9/2017 | Matsunaga et al. |
| 10,034,669 B2 | 7/2018 | Coleman et al. |
| 10,195,066 B2 | 2/2019 | Behan |
| 2003/0153935 A1 | 8/2003 | Mialhe |
| 2005/0273060 A1 | 12/2005 | Levy et al. |
| 2007/0123994 A1 | 5/2007 | Ortiz et al. |
| 2010/0036504 A1* | 2/2010 | Sobrino-Serrano ....... A61F 2/90 623/23.68 |
| 2010/0100109 A1 | 4/2010 | Stack et al. |
| 2015/0142049 A1 | 5/2015 | Delgado et al. |
| 2015/0374383 A1 | 12/2015 | Bödewadt et al. |
| 2017/0367711 A1 | 12/2017 | Bödewadt et al. |
| 2018/0271530 A1 | 9/2018 | Dayton et al. |
| 2018/0338849 A1 | 11/2018 | Behan |
| 2019/0099589 A1 | 4/2019 | Walsh et al. |
| 2019/0298559 A1* | 10/2019 | Gupta ................... A61B 5/061 |
| 2020/0268537 A1 | 8/2020 | Reisin et al. |
| 2021/0121179 A1 | 4/2021 | Ben-David et al. |

FOREIGN PATENT DOCUMENTS

| | | |
|---|---|---|
| WO | 2007038715 A1 | 4/2007 |
| WO | 2016096529 A1 | 6/2016 |

\* cited by examiner

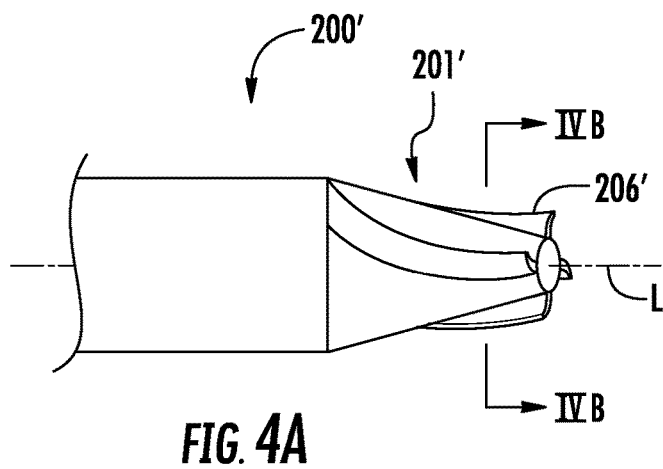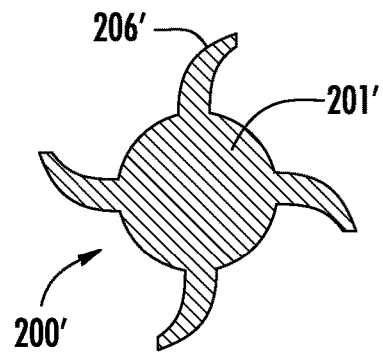
FIG. 4A  FIG. 4B
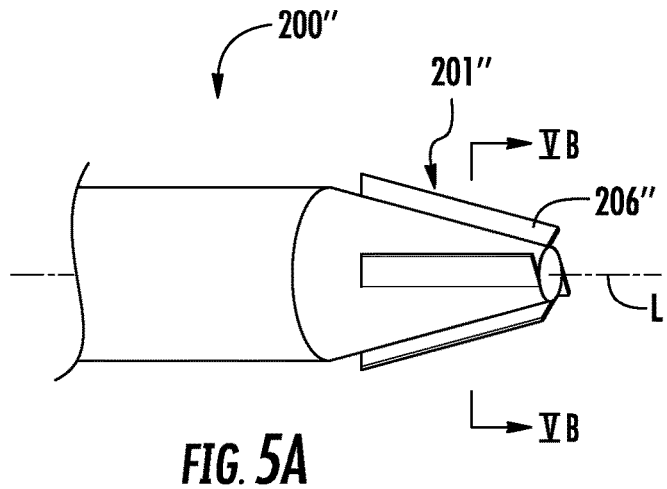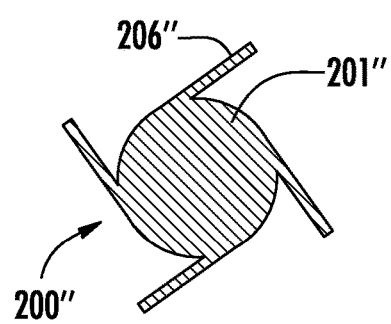
FIG. 5A  FIG. 5B
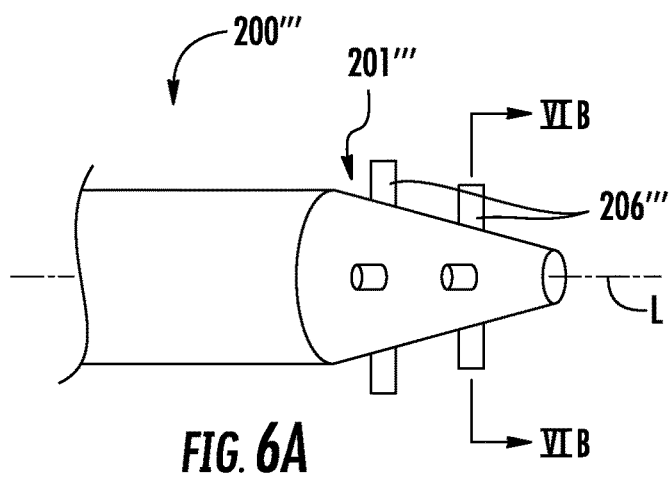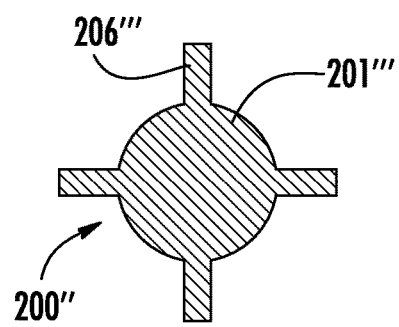
FIG. 6A  FIG. 6B

DEVICES, SYSTEMS, AND METHODS FOR ADJUSTING A PASSAGE THROUGH AN IMPLANTABLE DEVICE

CROSS-REFERENCE TO RELATED APPLICATIONS

This application claims the benefit of priority of U.S. Provisional Application No. 63/190,545, filed May 19, 2021, the entire disclosure of which is hereby incorporated by reference herein for all purposes.

FIELD

The present disclosure relates generally to the field of implantable medical devices, systems, and methods for adjusting accessibility through a passage of a medical device. More particularly, the present disclosure relates to devices, systems, and methods for controlling and/or changing a passage diameter or lumen in a flow-regulating device such as an occlusion device or a lumen-apposing device. Even more particularly, the present disclosure relates to devices, systems, and methods for controlling and/or changing a passage diameter in an implantable device to allow the medical device to selectively block or allow passage of materials therethrough.

BACKGROUND

Various implantable devices have been used to form anastomoses or to occlude passages or lumens within a patient's body. For instance, various metabolic treatments utilize stents advantageously with fully endoscopic procedures. The outcomes of such procedures sometimes are difficult to predict and may be inconsistent in effect due to the wide range of patient conditions and responses to the treatment. Adjustment of an implantable device may be desirable to adjust the device to modify the treatment for a variety of reasons, including simply to adjust during the course of treatment. Moreover, certain treatments result in closing off more direct pathways to other anatomical structure to which access (at least temporary access) may be later required.

Accordingly, there is a need for a device and accompanying system and procedure(s), which preferably may be fully endoscopic, that can be used to control and/or actively to tailor the configuration of a passage through an implantable device, such as to control or to tailor the flow of nutrients through the gastrointestinal (GI) tract, allowing physicians to personalize and adjust a patient's treatment (e.g., anastomosis or occlusion) to their particular needs, and/or to allow selective access to an anatomical site with otherwise reduced accessibility.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with an aspect of the present disclosure, a system for controlling the size of a passage through an implantable device includes an adjustable tubular device with an adjustable passage formed therethrough, and an elongated element extendable into the adjustable passage through the adjustable tubular device to increase the size of the adjustable passage.

In some embodiments, the adjustable tubular device has a first end, a second end, and an intermediate region therebetween, with at least the intermediate region being twisted into a closed configuration to close the adjustable passage through the adjustable tubular device. In some embodiments, the elongated element is a passage-opening device configured to untwist the twisted intermediate region of the adjustable tubular device. In some embodiments, the passage-opening device includes engagement features configured to engage with features of the twisted intermediate region of the adjustable tubular device. In some embodiments, the engagement features include a plurality of projections extending radially outwardly from a distal end of the elongated element. In some embodiments, the passage-opening device is a catheter.

In some embodiments, the elongated element includes engagement features configured to engage with features of the adjustable passage of the adjustable tubular device to increase the size of the adjustable passage.

In some embodiments, the adjustable tubular device is guided over the elongated element to a deployment site across an anatomical structure.

In some embodiments, the system further includes a lumen-controlling plug configured to fit within the adjustable passage of the adjustable tubular device to hold the adjustable passage in an open configuration.

In accordance with another aspect of the present disclosure, a system for adjusting the size of a passage through an implantable device includes an adjustable tubular device having an adjustable passage defined therethrough movable between a substantially closed configuration and an open configuration; and a first lumen-controlling plug configured to fit within the adjustable passage of the adjustable tubular device to hold the adjustable passage in a first open configuration.

In some embodiments, the system further includes a second lumen-controlling plug configured to fit within the adjustable passage of the adjustable tubular device to hold the adjustable passage in a second open configuration sized different from the first open configuration. In some embodiments, the second lumen-controlling plug is positionable within the first lumen-controlling plug.

In some embodiments, the first lumen-controlling plug is configured to mate with the adjustable tubular device to reduce shifting of the first lumen-controlling plug within the adjustable passage through the adjustable tubular device.

In some embodiments, the adjustable tubular device has a first retention member along a first end thereof and a second retention member along a second end thereof; and the first lumen-controlling plug has a first retention member configured to engage with the first retention member of the adjustable tubular device, and a second retention member configured to engage with the second retention member of the adjustable tubular device to resist shifting of the first lumen-controlling plug with respect to the adjustable tubular device.

In some embodiments, the system further includes an elongated element configured to open the adjustable passage of the adjustable tubular device to facilitate insertion of the first lumen-controlling plug therein. In some embodiments, the first lumen-controlling plug is guided over the elongated element and into the adjustable tubular device.

In accordance with another aspect of the present disclosure, a method of adjusting an implantable adjustable tubular device with an adjustable passage defined therethrough includes inserting an elongated element into the adjustable passage defined in the adjustable tubular device to open the adjustable passage; and inserting a lumen-controlling plug into the adjustable passage to hold open the adjustable passage.

In some embodiments, inserting the lumen-controlling plug includes guiding the lumen-controlling plug over the elongated element.

In some embodiments, the adjustable tubular device is twisted so that the adjustable passage therethrough is in a closed configuration, the method further including rotating the elongated element to untwist the passage of the adjustable tubular device.

In some embodiments, the method further includes engaging a feature of the lumen-controlling plug with a feature of the adjustable tubular device to inhibit shifting of the lumen-controlling plug within the adjustable passage of the adjustable tubular device.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 4A illustrates an example of an embodiment of a distal portion of a passage-opening device in accordance with various principles of the present disclosure.

FIG. 4B illustrates a cross-sectional view along line IVB-IVB of FIG. 4A.

FIG. 5A illustrates an example of an embodiment of a distal portion of a passage-opening device in accordance with various principles of the present disclosure.

FIG. 5B illustrates a cross-sectional view along line VB-VB of FIG. 5A.

FIG. 6A illustrates an example of an embodiment of a distal portion of a passage-opening device in accordance with various principles of the present disclosure.

FIG. 6B illustrates a cross-sectional view along line VIB-VIB of FIG. 6A.

DETAILED DESCRIPTION

Figure 1:
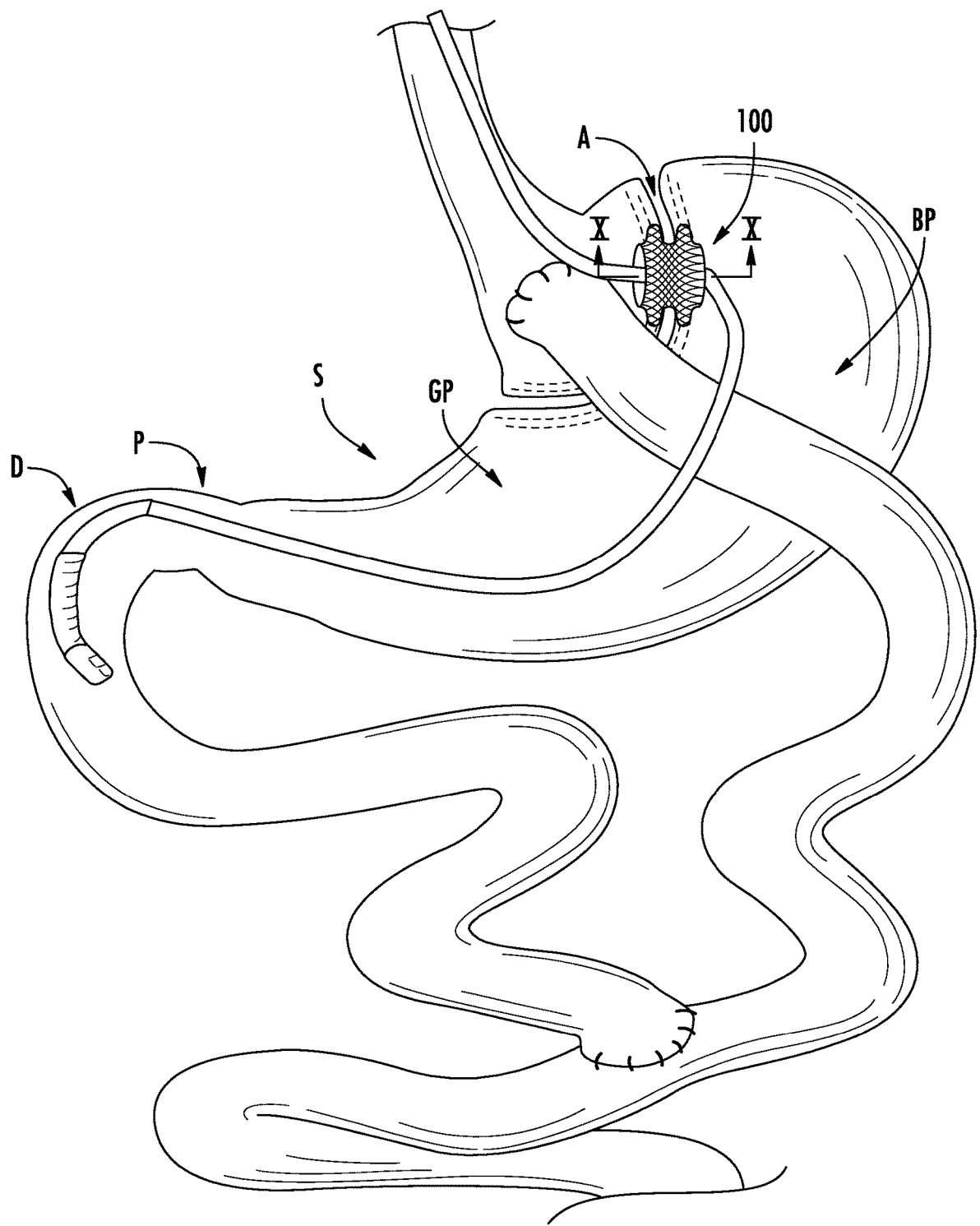
FIG. 1 illustrates a perspective view of an embodiment of an adjustable tubular device formed in accordance with various aspects of the present disclosure and positioned in a schematic representation of a gastrointestinal environment with an anastomosis between the stomach and a portion of the small intestines.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

In accordance with various principles of the present disclosure, an implantable device may be used to extend across an anatomical structure to control or regulate the size of a passage therethrough. For instance, an implantable device may extend across a body passage or lumen, such terms being used interchangeably herein without intent to limit. The body passage or lumen may include, without limitation, a portion of a passage or lumen, a passage or lumen between anatomical structures (passages, lumens, cavities, organs, etc.), a passage created across apposed tissue walls (such as to create an anastomosis) etc. The device has a passage or lumen (such terms being used interchangeably herein without intent to limit) therethrough which may be used to occlude or block or narrow or close or constrict or regulate or control (such terms and conjugations thereof may be used interchangeably herein without intent to limit) the body passage through which the device is positioned. The device may be considered and referenced as an occlusion or lumen-apposing or anastomosis or flow-regulating or flow-controlling device, and such terms and various other alternatives thereto may be used interchangeably herein without intent to limit. It will be appreciated that as used herein, reference will be made simply to an adjustable tubular device for the sake of convenience and without intent to limit. Moreover, reference to an adjustable portion of the adjustable tubular device is to be understood as reference to any portion of the adjustable tubular device which may be adjusted, such as to adjust the size (e.g., diameter) of a passage therethrough.

In accordance with various principles of the present disclosure, the size or diameter of the passage of an adjustable tubular device formed in accordance with various principles of the present disclosure is selectively adjustable between a closed (understood to include fully closed or substantially but not fully closed, such as greater than about 80% closed up to about 100% closed, including increments of 0.5% therebetween) configuration and an open configuration. The passage may be configured to be in a closed position when in a neutral/rest configuration (unaffected by another device or any action taken on the passage), and movable into an open position only upon active application of force or another action thereto. The open position may be selected or controlled or otherwise determined by the device used to open the passage and/or the manner in which the passage is moved to an open position. The passage may be opened to any of a variety of degrees of openness (e.g., the size of the opening is variable) to adjust the flow of materials (e.g., the volume, rate, amount, etc.) through the passage. For instance, the passage may simply be moved into an open configuration from an otherwise closed configuration. Alternatively or additionally, the passage may have a neutral open configuration and the passage may be stretched (e.g., enlarged or widened) beyond such neutral open configuration. For instance, the passage may be constricted from a neutral open configuration into a closed configuration, such as by being twisted or by application of a separate closure element thereto, and opened beyond such neutral open configuration into a stretched or widened configuration.

In some embodiments, an implantable device formed in accordance with various principles of the present disclosure is used as an occlusion device, and may be selectively moved to an open configuration if passage of materials through the otherwise occluded passage is desired or indicated. In some embodiments, an implantable device formed in accordance with various principles of the present disclosure is used to connect lumens or cavities or organs or other anatomical structures which are brought into apposition such as by the lumen-apposing device or another device (e.g., a separate lumen-apposing device), to create an anastomosis with an adjustable passage therebetween. Principles of the present disclosure may be applied to various treatment protocols and/or various medical procedures, such as if it may be desirable to adjust the rate of passage through a flow-restricting device and/or a portion thereof while still implanted in the patient.

Devices, systems, and methods in accordance with various principles of the present disclosure may be used with various gastric procedures which involve controlling or occluding flow of gastric materials from the stomach through the pylorus, such as bariatric treatments, or treatments of other gastrointestinal conditions. For instance, various protocols involve reducing and/or slowing the rate of passage of materials through the pylorus and/or occluding/excluding the pylorus from the stomach. An adjustable tubular device formed in accordance with various principles of the present disclosure may be structured to occlude (partially or fully/completely) flow therethrough and, consequently, flow of material through the pylorus. An adjustable tubular device formed in accordance with various principles of the present disclosure may also be used in bariatric treatments involving increasing the feeling of satiety in the patient, with the intent to reduce the desire to eat, with consequent reduction in caloric intake. Various approaches to increasing the feeling of satiety include increasing the time food remains in the stomach and/or reducing or slowing the rate of gastric emptying (the flow of material, such as fluids or chyme, from the stomach to the duodenum), with consequent inducement of a feeling of fullness or satiety which may lead to reduction of food intake and associated weight loss.

Other procedures involve selectively gaining access through walls of various parts of the anatomy, such as a tissue wall or apposed tissue walls. It may be desirable to form a passage through a tissue wall or apposed tissue walls and allow for such passage to be selectively opened or closed. For instance, a surgical bypass procedure may render an anatomical structure difficult to access, yet access to such structure may be desired or required after the bypass has been performed. One example is when a patient who has had a Roux-en-Y gastric bypass needs an endoscopic retrograde cholangiopancreatography (ERCP), there is no longer a direct path for a physician to access the papilla endoscopically. Physicians may create a temporary passage from the stomach pouch to the excluded stomach. This new passageway, although temporary (e.g., 3-4 weeks), can reduce the efficacy of the bariatric procedure by allowing gastric materials (e.g., chyme to pass through the bypassed portion of the GI tract. Depending on the disease being treated, multiple ERCP's may be needed to fully treat the patient's condition, further extending the time the passage is needed.

In accordance with various aspects of the present disclosure, an adjustable tubular device is formed with an adjustable portion with an adjustable passage therethrough. The adjustable passage can be selectively opened or closed during a procedure, allowing for temporary access or passage (of materials or medical devices or instruments) through the adjustable tubular device, or held open for a longer period of time (and allowed to be closed when desired or medically indicated). In some embodiments, the adjustable tubular device has a narrowed adjustable portion which is selectively expandable to allow passage of material therethrough when the passage is expanded. In some embodiments, a portion of the adjustable tubular device is twisted, such that the twist narrows or closes the passageway. Such twist in the adjustable tubular device may be modified or adjusted, e.g., untwisted, to modify or adjust the degree of closure or occlusion of the passageway created by such twist. In some embodiments, an elongated element is provided to extend through the passageway to adjust the adjustable portion of the adjustable tubular device. The elongated element may have a unique configuration to facilitate engagement with the configuration of the adjustable portion and may be referenced herein as a passage-opening device for the sake of convenience without intent to limit to a particular function. In some embodiments, the adjustable portion of the adjustable tubular device is narrowed or twisted into a substantially closed configuration and selectively adjustable to an at least partially open configuration such as untwisting. It will be appreciated that other configurations are within the scope and spirit of the present disclosure. In some embodiments, the passage-opening device may be shaped or configured or otherwise provided with features corresponding with the shape or contour or other features of the closed (e.g., twisted) portion of the adjustable tubular device. It will be appreciated that principles of the present disclosure extend beyond the examples of a twisted-closed device and untwisting of such device described in further detail below.

The adjustable tubular device may be formed from a plurality of strands or wires or filaments which may be braided or woven or twisted or wrapped or intertwined or knitted or looped (e.g., bobbinet-style) or knotted or otherwise formed into a self-supporting structure. Alternatively, the adjustable tubular device may be formed from a laser-cut tube or bonded elongated elements or another self-supporting structure. Such structure may be alternately referenced as a stent or framework or scaffold without intent to limit. The adjustable tubular device may be formed of a biocompatible metal or a polymeric material or an alloy. In some embodiments, the material is a shape-memory or heat formable material, such as a nickel-titanium alloy (e.g., Nitinol). In some embodiments, the passage-opening device includes various features to engage the narrowed portion of the adjustable tubular device and/or elements thereof (e.g., engage between wires forming the adjustable tubular device).

In some embodiments, an additional tubular device is provided to adjust the size of the passageway through the adjustable tubular device. For instance, the adjustable passageway of the adjustable tubular device may be increased in diameter and an additional tubular device inserted therein to hold open the passageway of the adjustable tubular device to an extent lesser than the fully-open extent of the passageway of the adjustable tubular device.

It is noted that, in some embodiments, opening of a closed (e.g., twisted closed) region of the device may effect other changes in the device, such as changes to the axial length or other dimensions or properties of the device. For example, in some embodiments, retention members are provided at ends of the device to hold tissue walls in apposition and/or to hold the device in place with respect to the anatomical site at which the device is deployed/positioned (e.g., to inhibit or prevent migration of the device). In various examples, opening of a closed region of the device may affect the position of either or both of the retention members (e.g., relative positions and/or orientations, such as an axial distance between the retention members) and/or the configuration of either or both of the retention members (e.g., the dimensions of the retention member, such as either or both of their diameters, which may be affected by the dimensions of other regions of the device, such as the region being adjusted). Adjustability of the configuration of a closed region of an implantable device to affect the retention members may be advantageous for affecting the holding force of the retention members on tissue walls contacted (e.g., held in apposition by) the retention members. Such adjustment may be independent of whether the device allows passage of materials therethrough. As such, if an additional device is inserted into (or otherwise modifies) an adjustable tubular device formed in accordance with various principles of the present disclosure to maintain an adjustment to the configuration of the adjustable tubular device other than the size of the passage through the adjustable tubular device, such additional device need not include a passage therethrough if passage of materials through the adjustable tubular device is not desired.

In accordance with various principles of the present disclosure, the adjustable tubular device may be sized and configured for transluminal or transcatheter or endoscopic delivery. As such, in accordance with an aspect of the present disclosure, the adjustable tubular device may be collapsed or otherwise reduced in cross-sectional dimension to fit through a tubular delivery device used in minimally-invasive procedures (in contrast with an open surgical procedure). The adjustable tubular device may expand once deployed. For instance, the adjustable tubular device may be formed to be self-expanding (and, in such case, advantageously formed of a shape memory material which expands the device once no longer held or constrained within a delivery device), or may be expanded with the assistance of another expandable device, such as an expandable balloon. To allow the option of removal from the deployment site, the adjustable tubular device may be formed to be selectively collapsible from its expanded deployed configuration, in any of various manners known or heretofore known in the art.

Turning now to the drawings, an adjustable tubular device 100 formed in accordance with various principles of the present disclosure is illustrated in FIG. 1 as positioned in one example of an environment in which principles of the present disclosure may be applied in a stomach S in which a Roux-en-Y gastric bypass or other type of bypass has been performed. As may be appreciated, the stomach S has been sectioned into a functional portion of the stomach S, which may be referenced as the gastric pouch GP, and the bypassed portion of the stomach BP, which generally is excluded or closed off from the passage of food along the digestive tract. More specifically, the bypassed portion of the stomach BP is the lower portion of the stomach S which normally passes food materials (e.g., chyme, partially digested food materials, etc.) into the duodenum D. The gastric pouch GP is connected directly with the jejunum J. As such, typical access through the pylorus P to the proximal region of the intestines, such as the duodenum D as well as the pancreas and pancreatic duct and bile duct, is cut off. If more ready access to such anatomical structures is desired, an anastomosis A into the bypassed portion of the stomach BP may be created with an adjustable tubular device 100 such as formed in accordance with principles of the present disclosure and as illustrated in FIG. 1. An adjustable tubular device 100 formed in accordance with principles of the present disclosure may be used in conjunction with other types of gastric bypass procedures, such as a gastrojejunostomy (not illustrated though readily understood to those of ordinary skill in the art, such as with reference to United States Patent Application Publication 2018/08271530, filed on Mar. 26, 2018, and published on Sep. 27, 2018, which published patent application is incorporated herein in its entirety for all purposes). Although it is generally desirable for the device forming the gastrojejunostomy in such procedure to remain open (and thus generally not a typical site for an adjustable tubular device 100 formed in accordance with principles of the present disclosure), it generally is still desirable to close off or to at least restrict access through the pylorus P to the duodenum D to promote the bypass to the jejunum J. An adjustable tubular device 100 formed in accordance with various principles of the present disclosure may be positioned across the pylorus P to effect the desired degree of closure of the pylorus P, while allowing selective adjustment of the degree of closure of the adjustable tubular device 100. Positioning of an adjustable tubular device 100 formed in accordance with various principles of the present disclosure to regulate flow through the pylorus P to regulate gastric emptying is yet another potential use of an adjustable tubular device 100 formed in accordance with various principles of the present disclosure.

Figure 2:
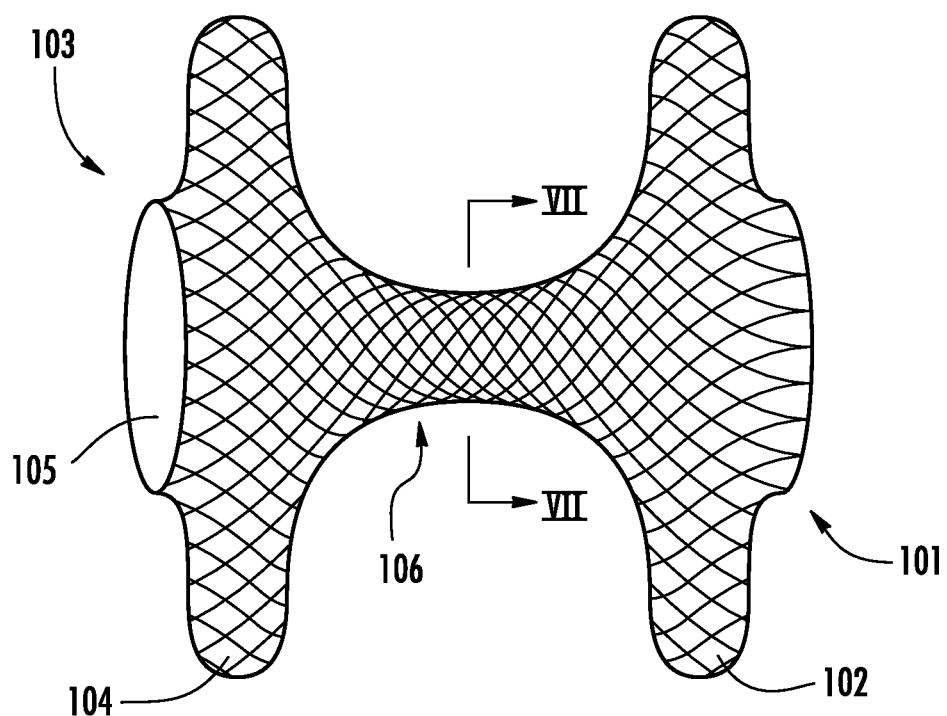
FIG. 2 illustrates an embodiment of an adjustable tubular device formed in accordance with various aspects of the present disclosure holding tissue walls in apposition and in a closed configuration.

As may be appreciated more readily with reference to FIG. 2, an example of an adjustable tubular device 100 formed in accordance with principles of the present disclosure has a first end 101, a second end 103, with a lumen 105 extending therebetween. The first end 101 may be widened to form a first retention member 102 and the second end 103 may be widened to form a second retention member 104. The retention members 102, 104 (which may alternately referenced as flanges without intent to limit) preferably are formed to be sufficiently wide and to have enough retention strength to hold the adjustable tubular device 100 in place, such as in accordance with various tissue-apposing devices or stents known or heretofore known in the art. The retention members 102, 104 may any of a variety of shapes, such as concave, convex, disc-shaped, cylindrical (e.g., having a longer longitudinal extent then illustrated), etc., or other configurations, the particular shape and configuration not being limited by the present disclosure. It will be appreciated that the lumen inner diameter need not be completely closed (i.e., have an inner diameter of 0 mm) when in a neutral configuration. Generally, the inner diameter of the lumen 105 when closed is less than 5 mm. The lumen 105 may be opened to a size allowing passage of a medical device or instrument therethrough, or for a desired volume or rate of flow of materials (e.g., bodily materials or ingested materials) therethrough. In some embodiments, the maximum inner diameter of the lumen 105 may be approximately 20 mm. In some embodiments, the diameter of the retention members 102, 104 may be at least about 30 mm and at most about 40 mm. The details of such features are not critical to the present disclosure and thus left to those of ordinary skill in the art to determine for a given environment in which an adjustable tubular device 100 is to be used.

As illustrated in FIG. 2, the intermediate region 106 of the adjustable tubular device 100 between the first end 101 and the second end 103 (which may be alternately referenced herein as a saddle region 106 without intent to limit) may be constricted to reduce the cross-sectional size (e.g., diameter) of the lumen 105 to affect (e.g., reduce or otherwise regulate) flow therethrough. In the illustrated example, the intermediate region 106 of the adjustable tubular device 100 is twisted to close the intermediate region 106. However, it will be appreciated that other constrictions are within the scope and spirit of the present disclosure, such as use of elastic bands or sleeves over the intermediate region 106 to constrict the portion of the lumen 105 extending therethrough (such elastic bands or sleeves being expandable to adjust the size of the lumen 105 in accordance with various principles of the present disclosure described in further detail below).

Figure 3A:
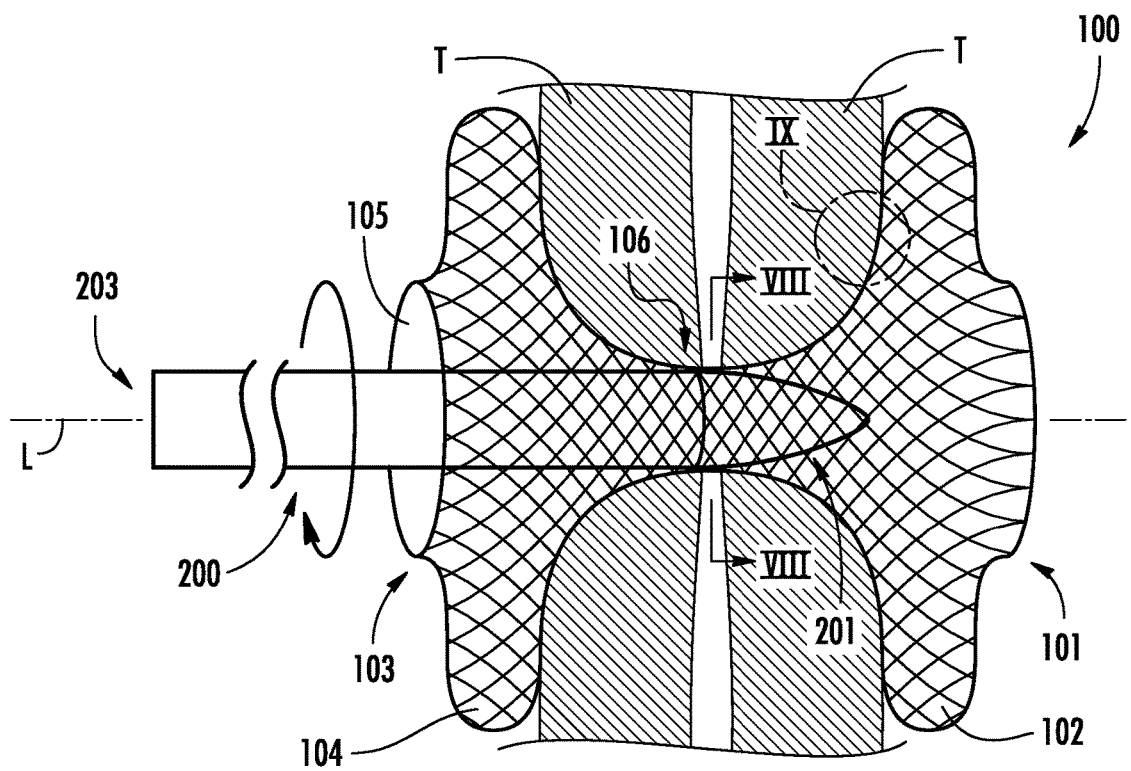
FIG. 3A illustrates an embodiment of an adjustable tubular device such as illustrated in FIG. 2, but with a passage-opening device being inserted therein.
Figure 3B:
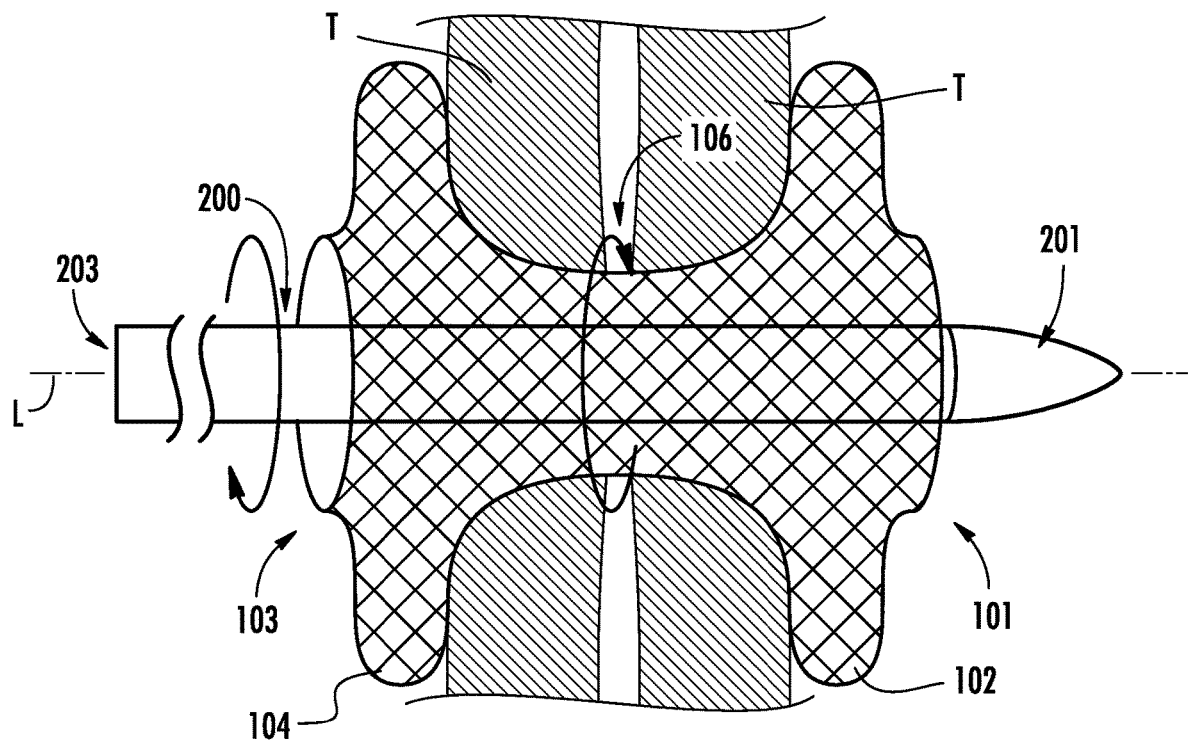
FIG. 3B illustrates a further position of a passage-opening device inserted within an adjustable tubular device as illustrated in FIG. 3A.

As illustrated in FIG. 3A and FIG. 3B, in accordance with an aspect of the present disclosure, an elongated element 200 may be inserted into one end of the adjustable tubular device 100 and into the lumen 105 of the adjustable tubular device 100 to expand the intermediate region 106 of the adjustable tubular device 100. It will be appreciated that the elongated element 200 generally is inserted into the end 101, 103 of the adjustable tubular device 100 which is more readily accessible. Thus, although the elongated element 200 is illustrated in FIG. 3A as being inserted into the second end 103, the elongated element 200 may instead be inserted into the first end 101. The distal end 201 of the elongated element 200 is inserted into the elongated element 200, with the proximal end 203 positioned for access by a medical professional to control advancement and manipulation of the elongated element 200. The elongated element 200 may extend proximally such that the proximal end 203 thereof is outside the patient and may be coupled to a control handle or the like. For instance, natural orifice transluminal endoscopic surgery (NOTES) may be used to adjust an adjustable tubular device 100 in accordance with various principles of the present disclosure, and the elongated element 200 may extend through the patient's esophagus proximally to extend out the mouth of the patient. Alternative points of entry and access to a treatment site, such as transluminal or vascular, are within the scope and spirit of the present disclosure. For instance, rectal access to an adjustable tubular device 100 used in the gastrointestinal system, or vascular access to an adjustable tubular device 100 used in the vascular system, are within the scope and spirit of the present disclosure. A guidewire (such as inserted through a lumen through the elongated element 200) may be used to assist with guiding the elongated element 200 to the adjustable tubular device 100. The distal end 201 of the elongated element 200 preferably is sufficiently strong in the longitudinal direction (e.g., has sufficient compressive resistance) to be advanced into the constricted adjustable portion of the intermediate region 106 of the adjustable tubular device 100 to adjust the size of the lumen 105 therethrough to consequently adjust the ability of materials to pass through the lumen 105 of the adjustable tubular device 100. For instance, the distal end 201 of the elongated element 200 may be reinforced with a braided coil or other structure (e.g., a composite structure) to enhance compressive resistance.

In an example of an embodiment of an adjustable tubular device 100 as illustrated in FIG. 2, in which the intermediate region 106 is twisted, the distal end 201 of the elongated element 200, illustrated in FIGS. 3A and 3B, preferably has sufficient torsional strength to untwist the twisted adjustable portion of the intermediate region 106 to adjust the amount or degree to which the lumen 105 through the adjustable tubular device 100 is opened. Various reinforcements such as described above may enhance torsional resistance of the elongated element 200. An elongated element 200 configured to adjust the lumen 105 of the example of an adjustable tubular device 100 illustrated in FIG. 2 is advanced (e.g., along a longitudinal axis L thereof) into the adjustable portion of the intermediate region 106, such as illustrated in FIG. 3A, and is rotated (e.g., about a longitudinal axis L thereof) to untwist the adjustable portion of the intermediate region 106, such as illustrated in FIG. 3B. It will be appreciated that other configurations of elongated elements corresponding to other configurations of adjustable portions of adjustable tubular devices formed in accordance with various principles of the present disclosure are within the scope and spirit of the present disclosure.

The distal end 201 of an elongated element 200 configured to untwist a twisted intermediate region 106 of an adjustable tubular device 100 may be provided with one or more engagement features structured and configured to engage with the twisted configuration of the intermediate region 106 of the adjustable tubular device 100 to untwist such configuration. For instance, the engagement features may be projections or ridges or grooves which engage with or between the twists of the twisted intermediate region 106. Various embodiments of examples of engagement features which may be provided on an elongated element 200 structured and configured to engage with a twisted intermediate region 106 of an adjustable tubular device 100 formed in accordance with principles of the present disclosure are illustrated in FIGS. 4A, 4B, 5A, 5B, 6A, 6B, 7A, 7B.

In the embodiment illustrated in FIGS. 4A and 4B, the distal end 201' of an example of an elongated element 200' has engagement features 206' in the form of longitudinal projections along the distal end 201' of the elongated element 200'. As may be appreciated with reference to FIG. 4A, the engagement features 206' twist (e.g., are helical or otherwise nonlinear) about the longitudinal axis L of the elongated element 200' such as to correspond to the twist in the adjustable tubular device 100 with which the elongated element 200' is to be used. As may be appreciated with reference to FIG. 4B, the engagement features 206' extend radially outwardly from the elongated element 200' and optionally are radially curved (e.g., circumferentially about the longitudinal axis L of the elongated element 200') at least along a portion thereof. In other words, the example of an embodiment of engagement features 206' illustrated in FIG. 4B extend radially outward from the distal end 201' of the elongated element 200' and are curved at least at a free end thereof (along the end or edge of the engagement features 206' furthest from the distal end 201' elongated element 200' and unattached thereto).

Instead of extending in a curved, such as a helical, direction about the distal end 201 of the elongated element 200, the engagement features 206 may extend substantially longitudinally along the longitudinal axis L of the elongated element 200, such as in the example of an embodiment of an elongated element 200" illustrated in FIGS. 5A and 5B. In particular, the engagement features 206" of the elongated element 200" are illustrated in FIG. 5A as extending substantially longitudinally along the longitudinal axis L of the elongated element 200". Additionally or alternatively, the engagement features 206" may extend radially way from the distal end 201" of the elongated element 200" in a generally straight direction, without curving as in the embodiment illustrated in FIG. 4B.

In the embodiment illustrated in FIGS. 6A and 6B, the distal end 201''' of an example of an elongated element 200''' has engagement features 206''' in the form of a plurality of individual projections spaced apart along the distal end 201''' of the elongated element 200'''. As may be appreciated with reference to FIG. 6A and FIG. 6B, the engagement features 206''' extend radially outwardly from the distal end 201''' of the elongated element 200'''. As may be appreciated with reference to FIG. 6A, the engagement features 206''' may be spaced apart from one another longitudinally along the longitudinal axis L of the elongated element 200'''. As may be further appreciated with reference to FIG. 6A, adjacent engagement features 206''' may be linearly and/or radially aligned with one another.

It will be appreciated that the engagement features 206 may be formed in any known or heretofore known manner in the art, such as molding, gluing, extrusion, machining, stamping, or cutting. The embodiment of FIGS. 5A and 5B illustrate, particularly in FIG. 5B, an example of engagement features 206 formed by cutting or quilling, in which cuts are formed in the face of the distal end 201" of the elongated element 200" (generally in a non-radial direction) and the cut is widened to draw apart a section into a projection (e.g., a quill or fin) forming the elongated element 200". It will further be appreciated that any number of engagement features 206 may be provided to engage the twisted portion of the adjustable tubular device 100. The shape or configuration or number of the engagement features 206', 206", 206''' is not limited to those illustrated and described herein.

Figure 7:
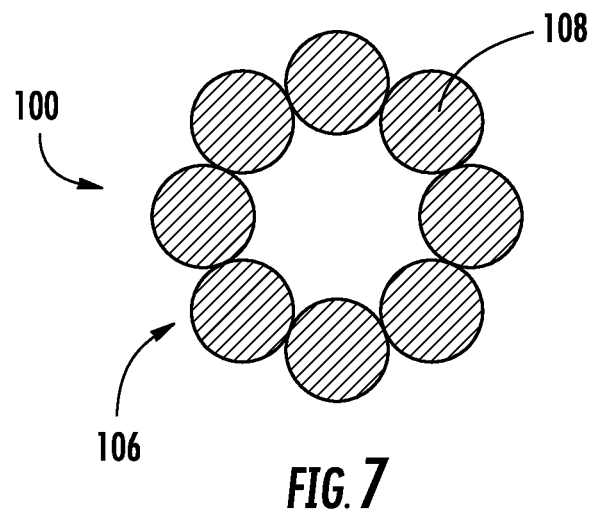
FIG. 7 illustrates an enlarged cross-sectional view along line VII-VII of FIG. 2.
Figure 8:
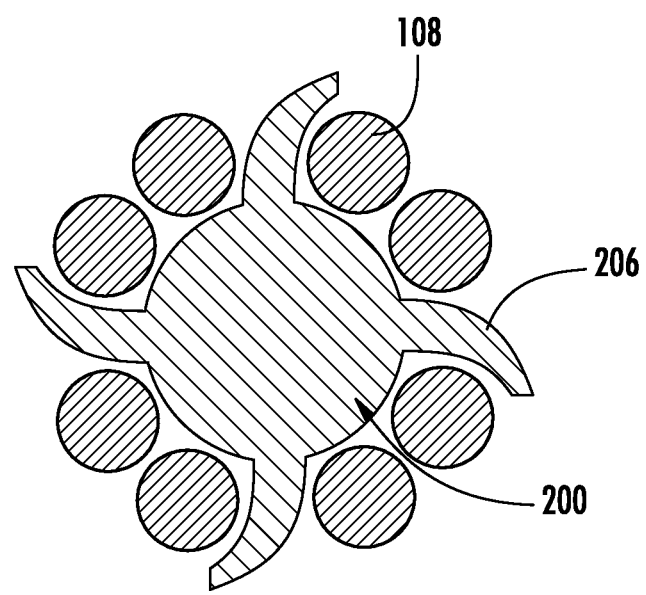
FIG. 8 illustrates an enlarged cross-sectional view along line VIII-VIII of FIG. 3B illustrating an example of an embodiment of a passage-opening device such as illustrated in FIG. 4A and FIG. 4B.

In some embodiments, the adjustable tubular device 100 is formed by a plurality of wires 108, such as may be appreciated from a schematic cross-sectional illustration of FIG. 7, taken along line VII-VII of FIG. 2. The one or more engagement features 206 may be configured to engage with the wires 108, such as with a one-to-one correspondence, or between groups of adjacent wires 108, such as illustrated in FIG. 8, showing a schematic cross-sectional view along line VIII-VIII of FIG. 3A. Fitting of the elongated element 200 within the lumen 105 causes the wires 108 (twisted and generally not parallel to the longitudinal axis L of the adjustable tubular device 100) to move apart (and to become more closely aligned with the longitudinal axis L of the adjustable tubular device 100), and twisting of the elongated element 200 moves the wires 108 even further apart to open the lumen 105.

Figure 9:
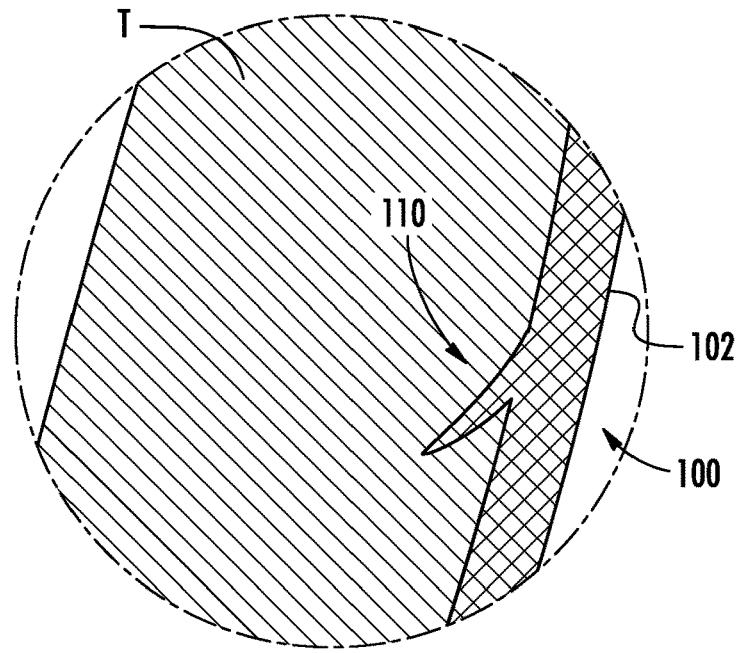
FIG. 9 illustrates a detail view of portion IX of the embodiment of an adjustable tubular device illustrated in FIG. 3A.

In some embodiments in which the adjustable portion of the adjustable tubular device 100 is twisted/untwisted, it may be desirable to hold a distal portion of the adjustable tubular device 100 with respect to the tissue or body passage across which the adjustable tubular device 100 is positioned. Various holding features 110 may be provided and/or formed on the adjustable tubular device 100 to engage and/or anchor the adjustable tubular device 100 with respect to the tissue or body passage. For instance, tissue-engaging projections (e.g., barbs, anchors, etc.), tissue ingrowth features, micropatterns, threads, and/or other mechanical or tissue-based locking features may be provided on a surface of the adjustable tubular device 100 to engage with tissue along which the adjustable tubular device 100 is deployed. In the embodiment of an adjustable tubular device 100 illustrated in FIGS. 3A and 3B, the adjustable tubular device 100 is shown holding tissue walls T in apposition (such as a stomach wall and the wall of the jejunum, if the adjustable tubular device 100 is positioned therebetween, as in FIG. 1). As may be appreciated with reference to the detail X of FIG. 3A illustrated in FIG. 9, at least one holding feature 110 (such as in the form of a tissue-engaging projection such as a barb) is on a surface of a retention member 102 abutting or engaging a tissue wall. The tissue wall may surround or be adjacent to the tissue across which the adjustable tubular device 100 is positioned. In the configuration of the illustrated example, the holding feature 110 is provided on a portion of the retention member 102 facing the intermediate region 106 (e.g., an inwardly-facing portion abutting or otherwise contacting one of the tissues held in apposition by the adjustable tubular device 100). However, it will be appreciated that other positions for the holding feature 110 are within the scope and spirit of the present disclosure, such as may be selected based on the environment in which or procedure with which the adjustable tubular device 100 is used. For instance, if the adjustable tubular device 100 is positioned across a body passage or lumen, such as a pylorus P, a holding feature 110 may be provided on a laterally-outwardly positioned portion of the adjustable tubular device 100 such as would engage the inner wall of a body passage in or across which the adjustable tubular device 100 is positioned. Generally, the at least one holding feature 110 is provided on a distal portion of the adjustable tubular device 100, such as on the distal retention member 102, so that the proximal portion of the adjustable tubular device 100 (generally more readily accessible by a medical professional) may be rotated while the distal portion of the adjustable tubular device 100 is held in place with respect to the body (e.g., tissue wall T).

Figure 10:
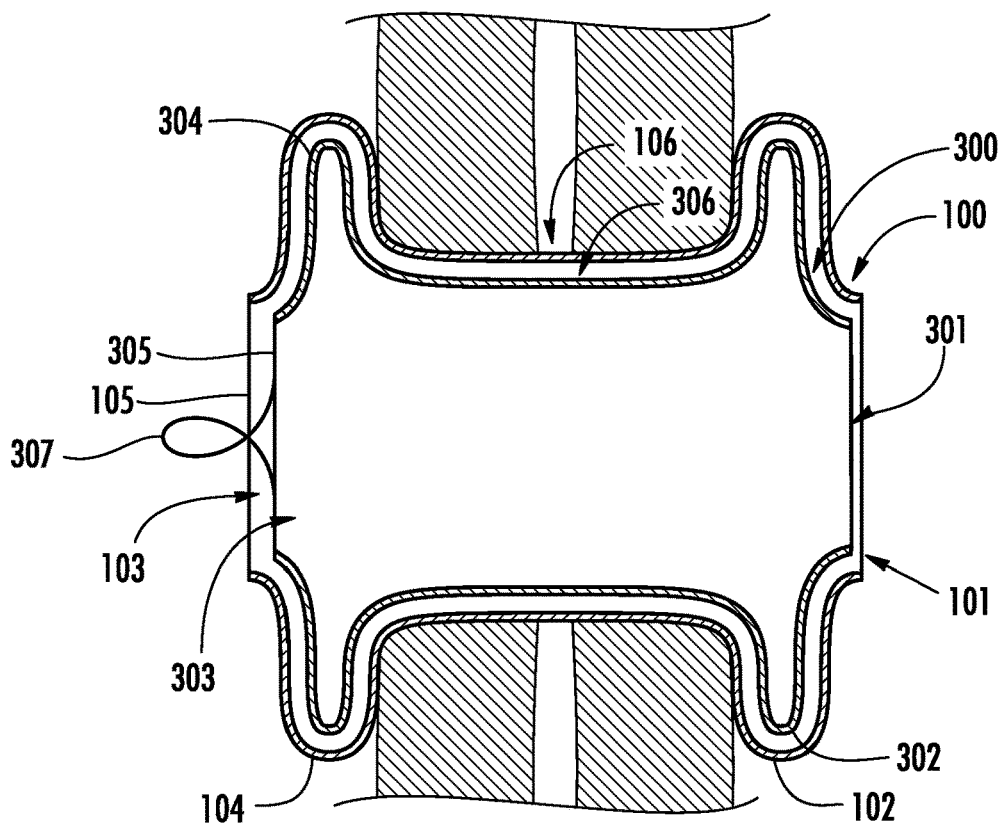
FIG. 10 illustrates a schematic cross-sectional view along line X-X of FIG. 1 illustrating an embodiment of a lumen-controlling-plug inserted within an embodiment of an adjustable tubular device, with details of the lumen-controlling-plug and adjustable tubular device walls not shown in order to enhance clarity of illustration.

In accordance with a separate and independent aspect of the present disclosure, as illustrated schematically in FIG. 10 (with certain features, such as details of the walls, left out for the sake of simplifying the illustration), an additional tubular element 300 may be positioned within the adjustable tubular device 100, once the lumen 105 of the adjustable tubular device 100 has been opened (such as by an elongated element 200 as described above), to maintain a desired opening through the lumen 105 of the adjustable tubular device 100. For the sake of convenience, to differentiate from the adjustable tubular device 100, the additional tubular element is referenced herein as a lumen-diameter-controlling-plug or lumen-controlling-plug 300. In some examples, the lumen-controlling-plug 300 may be deployed from a same or different device as used to deploy and/or position the adjustable tubular device 100 and/or a same or different device as used to open (e.g., untwist) the adjustable tubular device 100. For example, the lumen-controlling-plug 300 may be deployed using the elongate element 200 used to open the lumen 105 of the adjustable tubular device 100 such that opening of the adjustable tubular device 100 and a propping or plugging open of the same with the lumen-controlling plug 300 may be performed in a single step without prior removal of the elongate member 200 from within lumen 105. It will be appreciated that the term "plug" is used with reference to being positioned within (e.g., plugging or, more particularly, plugging open) the lumen 105 in which the lumen-controlling-plug 300 is positioned, such as to plug or, more particularly, to plug open the lumen 105.

The example of a lumen-controlling-plug 300 illustrated in FIG. 10 is shown extending through the lumen 105 of an adjustable tubular device 100 with a distal end 201 adjacent and somewhat spaced inwardly (towards the intermediate region 106) from the distal end 101 of the adjustable tubular device 100, and a proximal end 103 adjacent and somewhat spaced inwardly (towards the intermediate region 106) from the proximal end 103 of the adjustable tubular device 100. However, if desired, the length of the lumen-controlling-plug 300 may more closely match the length of the adjustable tubular device 100 so that the corresponding distal ends 101, 301 and proximal ends 103, 303 are closer together (e.g., substantially aligned) than as illustrated in FIG. 10. In the example of an embodiment illustrated in FIG. 10, the lumen-controlling-plug 300 is shaped and/or configured to mate or match or correspond with the shape and/or configuration of the adjustable tubular device 100 such as to reduce shifting (e.g., axial and/or radial relative movement) of the lumen-controlling-plug 300 within the adjustable tubular device 100. For instance, the embodiment of a lumen-controlling-plug 300 illustrated in FIG. 10 has a first retention member 302 configured to mate with (e.g., engage, correspond in shape, fit with, etc.) the first retention member 102 of the adjustable tubular device 100 and a second retention member 304 configured to mate with (e.g., engage, correspond in shape, fit with, etc.) the first retention member 104 of the adjustable tubular device 100. In the illustrated example, the retention members 302, 304 of the lumen-controlling-plug 300 fit within the spaced apart walls of the retention members 102, 104 of the adjustable tubular device 100, however other configurations are within the scope and spirit of the present invention. For instance, it will be noted that although the retention member 102, 104 of the adjustable tubular device 100 are illustrated as double-walled, the retention members 302, 304 of the lumen-controlling-plug 300 may be formed of single walls. Various manners of holding an inner stent within an outer stent may be used, such features not being critical to the basic principles of the present disclosure.

The diameter of the lumen 305 of the lumen-controlling-plug 300, such as the diameter of the intermediate region 306 of the lumen-controlling-plug 300, may be selected from a range of diameters depending on the intended course of treatment for which the adjustable tubular device 100 and lumen-controlling-plug 300 are provided/used. The lumen-controlling-plug 300 preferably has sufficient radial or hoop strength to withstand any constricting forces from an adjustable tubular device 100 configured to be closed in a rest position, along with any constricting forces from apposed tissue, such that the lumen-controlling-plug 300 can hold open the otherwise closed adjustable portion of the adjustable tubular device 100. In some embodiments, the lumen-controlling-plug 300 may have a higher radial or hoop strength than a corresponding adjustable tubular device 100. In some embodiments, a kit or system with more than one lumen-controlling-plug 300 is provided to allow adjustment of the size of the lumen 105 of the adjustable tubular device 100 at various stages during the course of treatment by inserting differently-sized lumen-controlling-plugs 300 within the lumen 105 of the adjustable tubular device 100. For instance, if an adjustable tubular device 100 formed in accordance with principles of the present disclosure is positioned to reduce the rate of flow of materials therethrough (e.g., positioned across a pylorus P in a bariatric procedure for reducing the rate of gastric emptying), it may be desirable to adjust the diameter of the lumen 105 of the adjustable tubular device 100 to adjust the rate of flow of materials depending on the patient's progress or responsiveness to the treatment. A lumen-controlling-plug 300 of a first diameter may be replaced with a lumen-controlling-plug 300 of a second different diameter. Additionally or alternatively, a first lumen-controlling-plug 300 with a lumen 305 having a first diameter may be initially inserted, and a second lumen-controlling-plug 300 with a lumen 305 having a second diameter smaller than the first diameter may be inserted into the first lumen-controlling-plug 300 to narrow the passage created by the first lumen-controlling-plug 300. Such set of lumen-controlling-plugs 300 with different diameters may be initially positioned together within the adjustable tubular device 100, with the second lumen-controlling-plug 300 removed if and when desired. Or, the first lumen-controlling-plug 300 may be positioned within the adjustable tubular device 100 and the second lumen-controlling-plug 300 positioned within the first lumen-controlling-plug 300 at a later time (e.g., hours, days, weeks, etc. later, depending on the course of treatment). Additionally or alternatively, the adjustable tubular device 100 may be left in the patient in a closed configuration and the lumen-controlling-plug 300 may be inserted into the lumen 105 of the adjustable tubular device 100 only for a procedure of limited duration, and removed once such procedure is complete, leaving in place the adjustable tubular device 100 in a once-again closed configuration. Because the size of instruments which may be passed through the adjustable tubular device 100 may vary depending on the procedure (e.g., based on the instruments to be passed through the adjustable tubular device 100), differently-sized lumen-controlling-plugs 300 may be provided for use with a given adjustable tubular device 100 to selectively open a passage within the body intended to be closed by the adjustable tubular device 100.

In order to deliver the lumen-controlling-plug 300 to the adjustable tubular device 100, the lumen-controlling-plug 300 may be passed over the elongated element 200 (e.g., the elongated element 200 may be passed through the lumen 305 of the lumen-controlling-plug 300) so that the lumen-controlling-plug 300 is mounted over the elongated element 200 to be delivered by the elongated element 200. Alternatively, the lumen-controlling-plug 300 may be delivered over another delivery device or mechanism as known or heretofore known in the art.

The lumen-controlling-plug 300 may be in the form of a braided stent, a laser-cut tubular stent, or any other configuration which allows for a compact delivery configuration thereof, yet expansion upon deployment within the adjustable tubular device 100 with sufficient stability to hold open the lumen 105 of the adjustable tubular device 100 as discussed above. A constricting feature 307, such as a suture or grasping loop or cinching cord or the like, such as known or heretofore known in the art, may be used to enhance removability. The configuration of such constricting feature is not critical to an understanding of the basic principles of the present disclosure and thus The elongated element 200 may have a passageway therethrough, such as for a guidewire facilitating guiding of the elongated element 200 to a treatment site. In some embodiments, the elongated element 200 is a catheter.

As noted above, various structures and features of the embodiments described herein and illustrated in the figures have several separate and independent unique benefits. Therefore, the various structures and features described herein need not all be present in order to achieve at least some of the desired characteristics and/or benefits described herein. Moreover, the various features described herein may be used singly or in any combination. It will be appreciated that various features described with respect to one embodiment may be applied to another embodiment, whether or not explicitly indicated. Thus, it should be understood that one or more of the features described with reference to one embodiment can be combined with one or more of the features of any of the other embodiments described herein. That is, any of the features described herein can be mixed and matched to create hybrid designs, and such hybrid designs are within the scope of the present disclosure. Therefore, the present invention is not limited to only the embodiments specifically described herein. The above descriptions are of illustrative examples of embodiments only, and are not intended as limiting the broader aspects of the present disclosure.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A system for controlling a size of a passage through an implantable device while implanted within a patient's body, said system comprising:
   an adjustable tubular device having a first end and a second end and shiftable from a collapsed configuration for delivery to an expanded deployed configuration with a twisted adjustable passage formed therethrough between the first end and the second end; and
   an elongated element extendable into the adjustable passage formed through said adjustable tubular device in the expanded deployed configuration and including engagement features configured to engage the adjustable passage, wherein said elongated element is rotatable within the adjustable passage with said engagement features engaged with the adjustable passage to untwist the twisted adjustable passage to increase the size of the adjustable passage to allow increased flow of material through the adjustable passage upon removal of said elongated element from the adjustable passage.

2. The system of claim 1, wherein the first end and the second end of the adjustable tubular device comprise an intermediate region therebetween, at least said intermediate region being twisted into closed configuration to close the adjustable passage therethrough.

3. The system of claim 2, wherein said elongated element is a passage-opening device configured to untwist said twisted intermediate region of said adjustable tubular device.

4. The system of claim 1, wherein said engagement features are radially-extending features configured to engage with features of the adjustable passage formed through said adjustable tubular device.

5. The system of claim 4, wherein said engagement features include a plurality of projections extending radially outwardly from a distal end of said elongated element.

6. The system of claim 3, wherein said passage-opening device is a catheter.

7. The system of claim 1, wherein said elongated element comprises engagement features configured to engage with features of the adjustable passage of said adjustable tubular device to increase the size of the adjustable passage.

8. The system of claim 1, wherein said adjustable tubular device is guided over said elongated element to a deployment site across an anatomical structure.

9. The system of claim 1, further comprising a lumen-controlling plug configured to fit within the adjustable passage of said adjustable tubular device to hold the adjustable passage in an open configuration.

10. A system for adjusting the size of a passage through an implantable device, said system comprising:
    an adjustable tubular device having an adjustable passage defined therethrough between a first end and a second end of said adjustable tubular device and having an inner diameter and movable between a substantially closed configuration and an open configuration with an increased inner diameter allowing flow of materials therethrough;
    an elongated element having engagement features configured to engage the adjustable passage formed through said adjustable tubular device, wherein said elongated element is rotatable within the adjustable passage with said engagement features engaged with the adjustable passage to increase the inner diameter of and open the adjustable passage of said adjustable tubular device; and
    a first lumen-controlling plug configured to fit within the passage of said adjustable tubular device opened by said elongated element to hold the adjustable passage in a first open configuration.

11. The system of claim 10, further comprising a second lumen-controlling plug configured to fit within the adjustable passage of said adjustable tubular device to hold the adjustable passage in a second open configuration with an inner diameter sized different from the first open configuration.

12. The system of claim 11, wherein said second lumen-controlling plug is positionable within said first lumen-controlling plug.

13. The system of claim 10, wherein said first lumen-controlling plug is configured to mate with said adjustable tubular device to reduce shifting of said first lumen-controlling plug within the adjustable passage through said adjustable tubular device.

14. The system of claim 13, wherein:
    said adjustable tubular device has a first retention member along a first end thereof and a second retention member along a second end thereof; and
    said first lumen-controlling plug has a first retention member configured to engage with said first retention member of said adjustable tubular device, and a second retention member configured to engage with said second retention member of said adjustable tubular device to resist shifting of said first lumen-controlling plug with respect to said adjustable tubular device.

15. The system of claim 10, wherein the elongated element is configured to open the adjustable passage of said adjustable tubular device to facilitate insertion of said first lumen-controlling plug therein.

16. The system of claim 15, wherein said first lumen-controlling plug is guided over said elongated element and into said adjustable tubular device.

17. A method of adjusting an implantable adjustable tubular device with a twisted adjustable passage defined therethrough between a first end and a second end of the implantable adjustable tubular device, said method comprising:
    inserting an elongated element into the twisted adjustable passage defined in the adjustable tubular device to engage engagement features of the elongated element with the twistable adjustable passage;
    rotating the elongated element with the engagement features engaged with the twisted adjustable passage between the first end and the second end of the implantable adjustable tubular device to untwist and open the adjustable passage; and
    inserting a lumen-controlling plug into the adjustable passage to hold open the adjustable passage.

18. The method of claim 17, wherein inserting the lumen-controlling plug comprises guiding the lumen-controlling plug over the elongated element.

19. The method of claim 17, further comprising rotating the elongated element, with the engagement features engaged with the twisted adjustable passage between the first end and the second end of the implantable adjustable tubular device, to adjust the diameter of the twisted adjustable passage to adjust the rate of flow of materials through the passage.

20. The method of claim 17, further comprising engaging a feature of the lumen-controlling plug with a feature of the adjustable tubular device to inhibit shifting of the lumen-controlling plug within the adjustable passage of the adjustable tubular device.

* * * * *